| United States Patent [19] | [11] Patent Number: 4,845,088 |
| Doherty et al. | [45] Date of Patent: Jul. 4, 1989 |

[54] TETRAZOLYL DERIVATIVES OF BETA-LACTAMS USEFUL AS ELASTASE INHIBITORS

[75] Inventors: James B. Doherty, New Milford; William K. Hagmann, Westfield; Paul E. Finke, Milltown; Shrenik K. Shah, Metuchen, all of N.J.

[73] Assignee: Merck & Co., Inc., Rahway, N.J.

[21] Appl. No.: 58,718

[22] Filed: Jun. 5, 1987

Related U.S. Application Data

[62] Division of Ser. No. 750,432, Jul. 1, 1985, Pat. No. 4,699,904.

[51] Int. Cl.$^4$ .................. C07D 501/00; A61K 31/545
[52] U.S. Cl. .................................... 514/202; 514/204; 540/222; 540/223
[58] Field of Search ................ 540/222, 223; 514/202, 514/204

[56] References Cited

U.S. PATENT DOCUMENTS 4,045,436 8/1977 Barth .................................... 540/223
4,699,904 10/1987 Doherty et al. .................... 540/222

FOREIGN PATENT DOCUMENTS 1520479 10/1975 United Kingdom .
1520480 10/1975 United Kingdom .

*Primary Examiner*—Nicholas S. Rizzo
*Attorney, Agent, or Firm*—Kevin J. McGough; Theresa Y. Cheng; Michael C. Sudol

[57] ABSTRACT

Tetrazolyl derivatives of β-lactams are found to be potent elastase inhibitors and thereby useful anti-inflammatory/antidegenerative agents.

8 Claims, No Drawings

TETRAZOLYL DERIVATIVES OF BETA-LACTAMS USEFUL AS ELASTASE INHIBITORS

This is a division of application Ser. No. 750,432 filed July 1, 1985, now U.S. Pat. No. 4,699,904.

BACKGROUND OF THE INVENTION

We have found that tetrazolyl derivatives of β-lactams such as cephalosporins and penicillins are anti-inflammatory/antidegenerative agents. potent elastase inhibitors and therefore useful Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelburg, New York, pp. 196–206, 1979.

Accordingly, an object of this invention is to discover new protease inhibitors, especially elastase inhibitors, useful for controlling tissue damage and various inflammatory or degenerative conditions mediated by proteases particularly elastase.

Another object of the present invention is to provide pharmaceutical compositions for administering the active tetrazolyl compounds as protease inhibitors.

Still a further object of this invention is to provide a method of controlling inflammatory conditions by administering a sufficient amount of one or more of the active, tetrazolyl compounds in a mammalian species in need of such treatment.

DETAILED DESCRIPTION OF THE INVENTION

This invention relates to tetrazolyl derivatives of β-lactams as potent elastase inhibitors useful in the prevention, control and treatment of inflammatory conditions especially arthritis and emphysema.

Some of the tetrazolyl derivatives are known antibiotics which have been described in U.S. Pat. Nos. 4,179,511; 4,105,668; 3,966,719; ,045,436; and DT No. 2,546,503.

The active compounds of the present invention are of formula:

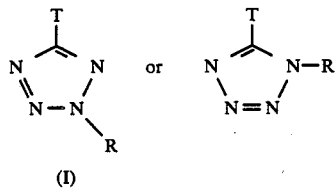

(I)

wherein T is

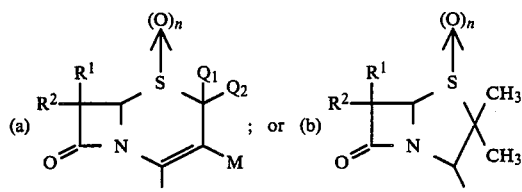

wherein n is an integer of 0 to 2;

M is:
(1) hydrogen;
(2) trifluoromethyl;
(3) chloro or fluoro;
(4) —COOH;
(5) —CHO; or
(6) —CH$_2$A wherein A represents
 (a) hydrogen
 (b) halo especially Cl, F, or Br;
 (c) —OR$_a$ wherein R$_a$ represents
  (1) H;
  (2) straight or branched chain alkyl having from 1 to 20 carbon atoms especially methyl, trifluoromethyl, ethyl, isopropyl, t-butyl, pentyl or hexyl;
  (3) aryl having from 6 to 10 carbon atoms especially phenyl, substituted phenyl or naphthyl;
  (4) cycloalkyl having from 3 to 8 carbon atoms especially cyclopentyl, or cyclohexyl;
  (5) alkenyl having from 2 to 20 carbon atoms especially C$_{2-6}$ alkenyl such as vinyl, allyl, or butenyl;
  (6) cycloalkenyl having from 5 to 8 carbon atoms especially cyclopentenyl or cyclohexenyl;
  (7) alkynyl having from 2 to 20 carbon atoms especially C$_{2-6}$ alkynyl for example, ethynyl, propynyl or hexynyl;
  (8) aralkyl, alkaryl, aralkenyl, aralkynyl, alkenylaryl or alkynylaryl wherein alkyl, aryl, alkenyl and alkynyl are as previously defined;
  (9) monoheteroaryl, di- or polyheteroaryl, or fused heteroaryl containing from 1 to 3 of any one or more of the heteroatoms N, S or O in each heteroaryl ring thereof, for example, pyridyl, pyrryl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbozolyl, isoxazolyl and the like;
  (10) heteroarylalkyl such as 2-pyridylmethyl, 2-thienylmethyl and 3-isothiazolylethyl; or
  (11) heterocycloalkyl e.g., 1,3-dioxacyclohex-4-11, piperidino, morpholino, oxacyclopropyl, pyrrolidino, tetrazolo, benzothiazolo, imidazolidino, pyrazolidino, and piperazino;
  (12) heterocycloalkenyl such as pyrrolino, 2-imidazolino, 3-pyrazolino or isoindolino;
  (13) halo loweralkyl especially halo-C$_{1-6}$ alkyl, for example, CF$_3$-; or
  (14) akenylalkyl.

The above groups (1)–(14) can be unsubstituted or can be substituted by radicals such as hydroxy, nitro C$_{1-6}$ alkyl, C$_{1-6}$ alkoxy, C$_{1-6}$ alkanoyl, C$_{1-6}$ alkanoyloxy, halo such as fluoro, chloro, bromo or iodo, cyano, carboxy,

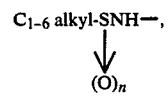

carbamoyl,

(wherein n is 0, 1 or 2), e.g., C$_{1-6}$ alkylsulfonyl, azido, carbamoyloxy, carboxamido, amino, substituted amino such as monoalkylamino and dialkylamino, haloalkyl, carboxyalkyl, carbamoylalkyl, N-substituted carbamoylalkyl such as N-methylcarbamoylmethyl, guanidino, N-substituted guanidino, guanidinoalkyl, and the like;

(d) R$_a$—CO—;
(e) R$_a$—CO—O for example, acetoxy, phenylcarbonyloxy, succinoyloxy, and benzylcarbonyloxy;
(f) R$_a$—O—CO—O for example, methoxycarbonyloxy;
(g)

for example —SH, CH$_3$S—, phenylthio, benzylthio, and heterocyclothio especially

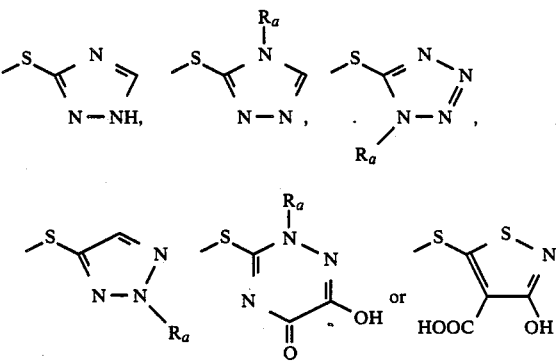

(h) $R_a$—O—CO—, for example, phenyloxycarbonyl or naphthyloxycarbonyl;

(i) $R_a$—CS—O—;

(j) $R_a$—CO—S—;

(k) $R_aR_bN$—CO—O— wherein $R_b$ is defined as $R_a$ but can be the same or different from $R_a$;

(l) $R_aR_bN$—CO—S—;

(m) $R_aR_bN$—, for example, —$NH_2$, —$N(CH_3)_2$, N-(2-chloroethyl)amino; $R_a$ and $R_b$ may join together and form part of the heterocyclic system, for example,

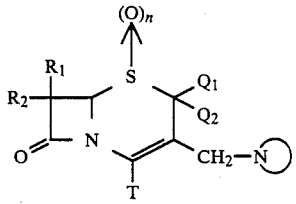

wherein

represents a nitrogen-containing heterocycle and its derivatives such as 5-cyanotriazol-1-yl, 4-methoxycarbonyltetrazol-1-yl;

(n) $R_a$—CO—$NR_b$—, for example, acetamido;

(o) $R_aR_bN$—CO—$NR_c$—, wherein $R_c$ is defined as $R_b$ and can be the same as or different from $R_b$, for example, carbamoylamino;

(p) $R_aR_bN$—CO—;

(q) —$NR_aR_bR_c$ such as —$N^+H_3$, —$N^+(C_2H_5)_3$ or —$N^+H(C_3H_7)_2$; or $R_a$, $R_b$, $R_c$ may join together and form part of a heterocyclic system such as pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)-pyridinium, 4-(N-carbomethoxycarbamoyl)-pyridinium, 4-(N-cyanocarbamoyl)pyridinium, 4-carboxymethylpyridinium, 4-hydroxymethylpyridinium, 4-trifluoromethyl-pyridinium, quinolinium, picolinium and lutidinium.

Preferably, A is:
(a) $R_a$—CO—O, for example, acetoxy and benzoyloxy;
(b) $R_aR_bN$—CO—O—, for example, benzylaminocarbonyloxy and N,N-dimethylaminocarbonyloxy;
(c) $R_aO$—CO—$CH_2NR_b$—CO—O—, for example, (p-methylbenzyloxycarbonyl)methylaminocarboxy, carboxymethylaminocarboxy or methoxycarbonylmethylaminocarboxy;
(d)

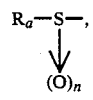

for example,

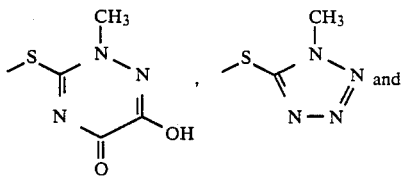

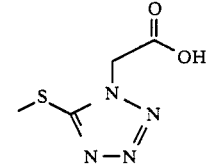

Representative of the $CH_2A$ groups are methoxymethyl, n-propoxymethyl, methylthiomethyl, acetoxymethyl, propionyloxymethyl, benzoyloxymethyl, (p-chlorobenzoyl)oxymethyl, succinoyloxymethyl, (p-methylbenzoyl)oxymethyl, pivaloyloxymethyl, (1-adamantyl)-carboxymethyl, butanoyloxymethyl, carbamoyloxymethyl, (N-methylcarbamoyl)oxymethyl, (N-ethylcarbamoyl)oxymethyl, [N-(2-chloroethyl)carbamoyl]oxymethyl, (N-phenylcarbamoyl)oxymethyl, [N-(carboxymethyl)-carbamoyl]oxymethyl, (N-p-hydroxy- sulfonylphenyl-carbamoyl)oxymethyl, p-carboxymethylphenylcarbamoyloxymethyl, methoxycarbonyloxymethyl, isobutanoyloxymethyl, cyclobutylcarbonyloxymethyl, carbamoylthiomethyl, (ethoxythiocarbonyl)thiomethyl, (n-propoxythiocarbonyl)thiomethyl, (cyclopentanoxythiocarbonyl)thiomethyl, methylthiomethyl, N,N-diethylthiocarbamoylthiomethyl, N-methylpiperazinium-1-thiocarbonylthiomethyl, N,N-dimethyl- piperazinyl-1-thiocarbonylthiomethyl, 2-furoylthiomethyl, isothiouroniummethyl, (5-methyl-1,3,4-thiadiazol-2-yl)thiomethyl, p-tolylsulfonylthiomethyl, 2-benzothiazolothiomethyl, mesyloxymethyl, 1-methyl1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxy methyl, p-sulfocinnamoyloxymethyl and 1R:2S-epoxypropylphosphonyloxymethyl, aminomethyl, acetamidomethyl, carbamoylaminomethyl, N,N-dimethylaminomethyl, N-(2-chloroethyl)aminomethyl, 5-cyanotriazol-1-yl-methyl, 4-methoxycarbonyltriazol-1-ylmethyl.

More preferably, A is:
(a) $R_a$—CO—O especially

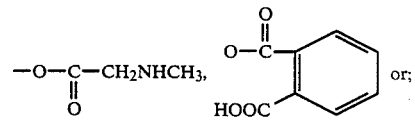

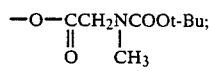

(b) $R_aHN$—CO—O, especially benzylaminocarbonyloxy; N,N-dimethylaminocarbonyloxy, or L- or D- form of

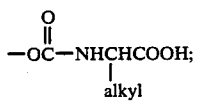

(c) $R_aO-CO-CH_2NH-CO-O-$ wherein $R_a$ is H, benzyl or $C_{1-6}$ alkyl;
(d) $R_a-S-$ as defined previously.

$R^1$ is:
(a) hydrogen;
(b) $R_a$;
(c)

(d) $R_aO-$;
(e) $R_a-CO-O-$;
(f) $R_a-CO-S-$;
(g) cyano;
(h) $-SO_3H$;
(i) $-SO_2NR_fR_g$ wherein $R_f$ and $R_g$ are as defined below;
(j) $-O-CO-OR_e$ wherein $R_e$ is as defined below;
(k) $-O-CO-SR_e$;
(l) $-O-CO-NR_e$;
(m) halo;
(n) $R_d(C=Z)-$ wherein Z is oxygen or sulfur, and $R_d$ is hydrogen, halo, hydroxy, $R_a-S-$, $R_aR_bN-$, alkyl, aryl, aralkyl, $R_aO$, such as benzyloxy, alkoxy or aryloxy, for example, phenoxy, pyrroloxy, furyloxy, and thienyloxy, alkylthio or arylthio; Examples of these substituents are $-COR_e$, $-COOR_e$, $-COSR_e$, $-CSSR_e$, $-CONH_2$, $-CSNH_2$, $-CSR_e$, $-CONHR_e$, $-CSNHR_e$, $-CONR_fR_g$ and $-CSNR_fR_g$ wherein $R_e$ represents H, a straight or branched chain alkyl group or haloalkyl group of 1-6 carbon atoms, aryl or aralkyl as previously defined, and $R_f$ and $R_g$ represent $R_e$ and can be the same as or different from $R_e$;
(o)

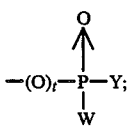

where t is 0 or 1, Y and W are the same or different and represent $R_e$, $-OR_e$, $-NR_fR_g$,

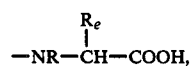

$-NR_2-NR_fR_g$, $-NR_2N=CR_fR_g$,

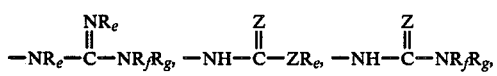

$-NC=Z$, $-OCOR_e$ and $-N_3$;
(p) $R^3NH-$, wherein $R^3$ represents:
(1) an acyl group of formula

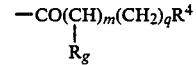

where m and q independently are integers of 0 to 4, $R^4$ is $R_a$ or $R_aE$ where $R_a$ is as previously defined, and E is $-O-$, $-S-$, or $-NH-$, for example:

(i) when both m and q are zero, the acyl group can be represented as $R_a-CO-$, or $R_aO-CO-$. Representative examples of such acyl groups that might be mentioned are those wherein $R_a$ is methoxy, ethoxy, benzyl, p-hydroxybenzyl, 3- or 4-nitrobenzyl, p-aminobenzyl, o-aminobenzyl, m-aminobenzyl, o-methylsulfonyl-, o-methylsulfinyl- or p-methylthio-benzyl, p-carboxymethylbenzyl, p-carbamoylmethylbenzyl, m-fluorobenzyl, m-bromobenzyl, p-chlorobenzyl, p-methoxybenzyl, p-aminomethylbenzyl, hydrogen, methyl, ethyl, cyanomethyl, 2-pentenyl, n-amyl, n-heptyl, phenethyl, difluoromethyl, trifluoromethyl, dichloromethyl, dibromoethyl, 1-(3-methylimidazolyl)methyl, 2- or 3-(5-carboxymethylthienyl)methyl, 2- or 3-(4carbamoylthienyl)methyl, 2- or 3-(5-methylthienyl)methyl, 2or 3-(5-methoxythienyl)methyl, 2- or 3-(4-chlorothienyl)methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, and tetrazolylmethyl.

(ii) when m is zero, the acyl group can be represented by the formula

Representative members of the substituent $-(CH_2)_1ER_a$ are allylthiomethyl, allylaminomethyl, phenylthiomethyl, butylmercaptomethyl, α-chlorocrotylmercaptomethyl, phenoxymethyl, phenylaminomethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, (p-(carboxymethyl)-phenoxy)methyl, (p-(carboxymethyl)phenylthio)methyl, 2-thiazolylthiomethyl, (p-(methylthio)phenoxy)methyl, (o-(methylsulfinyl)phenylthio)methyl, (p-(carboxy)phenoxy)methyl, (m-(carboxy)phenylthio)methyl, (p-(carboxymethyl)phenoxy)methyl, (o-(carboxymethyl)phenylthio)methyl, 2-pyrimidinylthiomethyl, phenethylthiomethyl, 1-(5,6,7,8-tetrahydronaphthyl)oxomethyl, 6,8-bis(methylthio)octanoyl.

(iii) when q is zero, the acyl group can be represented by the formula

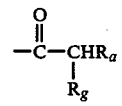

wherein $R_a$ is defined as above and $R_g$ is a radical such as amino, hydroxy, azido, carbamoyl, guanidino, alkanoyloxy, halo, $C_{1-6}$ alkylsulfonylamino, tetrazolyl, $C_{1-6}$ alkylsulfinyl or $C_{1-6}$-alkylthio, carboxy, carbalkoxy, and the like. Representative members of the substituent

are α-aminobenzyl, α-amino-2-thienyl, α-methyl-aminobenzyl, α-amino-β-methylthiopropyl, α-amino-3 or 4-chlorobenzyl, α-amino-3 or 4-hydroxybenzyl, α-amino-2,4-dichlorobenzyl, α-amino-3,4dichlorobenzyl, D(−)-α-hydroxybenzyl, α-carboxybenzyl, α-amino-3-thienyl, α-amino-2-thienyl, D(−)-α-amino-3-chloro-4-hydroxybenzyl, D(−)-α-amino-3-thienyl, 1-aminocyclohexyl, α-(5-tetrazolyl)benzyl, α-aminosulfonylbenzyl, α-methylsulfonylamino-3-thienyl, α-(N-methylsulfonylamino)benzyl, D(−)-α-guanidino-2-thienyl, D(−)-α-guanidinobenzyl, α-guanylureidobenzyl, α-hydroxybenzyl, α-azidobenzyl, α-fluorobenzyl, 4-(5-methoxy-l,3-oxadiazolyl)oxymethyl)aminomethyl, 4-(5-methoxy-l,3-oxazolyl)hydroxymethyl, 4-(5-methoxy-1,3-oxadiazolyl)carboxymethyl, 4-(5-methoxy-l,3-thiazolyl)aminomethyl, 4-(5-methoxy-1,3-thiazolyl)hydroxymethyl, 4-(5-methoxy-l,3-thiazolyl)carboxymethyl, 2-(5-chlorothienyl)-aminomethyl, 2-(5-chlorothienyl)hydroxymethyl, 2-(5-chlorothienyl)carboxymethyl, 3-(1,2-thiazolyl)aminomethyl, 3-(1,2-thiazolyl)hydroxymethyl, 3-(1,2thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, 2-azidooctyl-3-phenyl-3-azidomethyl, α-hydroxysulfonylbenzyl, and α-phosphonobenzyl.

(2) $R_aSO_2$—, for example, $R_aSO_2NH$— can be unsubstituted or substituted alkyl or aryl sulfonamido group such as benzenesulfonamido, ethylsulfonamido, trifluoromethylsulfonamido, phenylmethanesulfonamido, 2,5-dimethylbenzenesulfonamido, 4-chlorobenzenesulfonamido, 4-methoxybenzenesulfonamido, and the like;

(3) $R_aSO_2(CH(R_e))_k$, wherein k is 1-4, e.g., $CH_3SO_2CH(CH_3)$—, and $C_6H_5SO_2CH_2$—.

Preferably, $R^3$ is
(1) hydrogen;
(2)

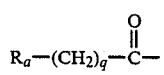

where $R_a$ represents:
(a) hydrogen;
(b) methyl or substituted methyl such as trifluoromethyl, cyanomethyl or methoxymethyl;
(c) thienyl;
(d) phenyl;
(e) mono- and disubstituted phenyl and thienyl wherein the substituents are selected from the group consisting of chloro, bromo, fluoro, nitro, $C_{1-6}$-alkyl, and $C_{1-6}$ alkoxy;

q is 0 or 1; and
(3)

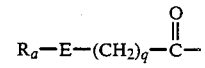

where E is oxygen or sulfur; $R_a$ and q are as previously defined.

Even more preferably, $R^3$ is

$R_a$ being selected from the group consisting of:
(1) trifluoromethyl;
(2) methyl;
(3) methoxy;
(4) hydrogen;
(5) benzyl;
(6) phenyl;
(7) 2-thienylmethyl;
(8) phenylthiomethyl;
(9) phenoxymethyl;
(10) benzyloxy; or
(11) $NCCH_2SCH_2$—.

In a preferred embodiment of this invention, $R^1$ is:
(a) —$OR_a$;
(b) $C_{1-6}$ alkyl;
(c)

(d) halo such as fluoro, chloro, bromo or iodo; or;
(e) hydrogen;
(f) $C_{6-10}$ aryl such as phenyl.
(g) $R_i$—CO—NH wherein $R_i$ is H, $C_{1-6}$alkyl or halo$C_{1-6}$alkyl;

In a more preferred embodiment of this invention $R^1$ is:
(a) $C_{1-3}$ alkyl;
(b) hydroxy;
(c) —$OR_a$ where $R_a$ is
  (1) $C_{1-6}$ alkyl especially methyl, ethyl, n-propyl;
  (2) —$C_6H_5$;
  (3) —$CH_2C_6H_5$;
  (4) —$CH_2CH_2C_6H_5$; or
  (5)

where $R_h$ represents hydrogen, $C_{1-6}$ alkyl, phenyl, substituted or unsubstituted benzyl, or $C_{1-6}$ alkylamino such as $CH_3NH$—, $C_2H_5NH$—;
(d) halo especially Cl or F;
(e) —$SO_2R_h$; or
(f) phenyl;
(g) halo$C_{1-6}$alkyl—CO—NH, e.g., $CF_3$—CO—NH—;
$R^2$ is (a) H;

(b) —O—$C_{1-6}$ alkyl especially —$OCH_3$;

(c) halo especially Cl or F; or (d) $C_{1-6}$alkyl;

preferably, $R^2$ is H.

$Q^1$ and $Q^2$ independently are:

(1) hydrogen;

(2) $C_{1-6}$ alkyl especially methyl, ethyl, isopropyl, n-pentyl or n-hexyl;

(3) halo $C_{1-6}$alkyl especially chloro or fluoro $C_{1-6}$alkyl; or (4) hydroxy $C_{1-6}$alkyl;

(5) methylene or substituted methylene especially $C_{1-6}$ alkylmethylene, unsubstituted or substituted phenylmethylene phenylthiomethylene, phenylsulfinylmethylene or phenyl sulfonylmethylene;

(6) $C_{1-6}$alkoxy $C_{1-6}$ alkyl;

(7) aralkyl especially unsubstituted or substituted benzyl or phenethyl;

(8) unsubstituted or substituted phenylthio-$C_{1-6}$alkyl, phenylsulfonyl $C_{1-6}$;

(9) unsubstituted or substituted phenoxy-$C_{1-6}$alkyl;

(10) unsubstituted or substituted phenylamino-$C_{1-6}$alkyl; or

(11) —$CH_2$—CO—O—$R_h$;

Preferably $Q^1$ and $Q^2$ independently are:

(1) hydrogen;

(2) $C_{1-6}$alkyl;

(3) substituted or unsubstituted methylene;

(4) unsubstituted or substituted phenylthio $C_{1-6}$alkyl or phenylsulfonyl $C_{1-6}$alkyl;

(5) aralkyl; or (6) —$CH_2$—CO—$OR_h$.

Even more preferably, $Q^1$ and $Q^2$ independently are:

(1) hydrogen;

(2) methyl, ethyl or i- or n-propyl;

(3) methylene;

(4) phenylthiomethyl or phenylsulfonyl methyl;

(5) benzyl;

(6) t-butoxycarbomethyl or carboxymethyl;

R is $R_a$;

Preferably, R is:

(a) H;

(b) phenyl or substituted phenyl such as p-methylphenyl or p-methoxyphenyl;

(c) benzyl of formula:

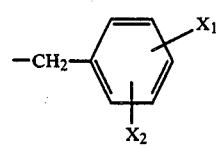

wherein $X_1$, $X_2$ independently are H, $OCH_3$, —COOH, $C_{1-6}$ alkyl, —$COOC_{1-6}$ alkyl, —$CH_2COOH$, —$CH_2COOC_{1-6}$ alkyl and the like.

The compounds of the present invention can be prepared from known β-lactam carboxylic acids such as those described in U.S. Pat. Nos. 4,459,405; 4,297,488; 4,260,598; 4,316,842; 4,035,359 and 4,234,579.

To obtain the 4-tetrazolyl derivatives of formula

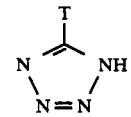

the cephalosporin- or penicillin-4-carboxylic acids are converted to the corresponding amides via conventional methods well-known in the art, for example, treatment of an acid with an amine in the presence of a good dehydration agent, e.g., dicyclohexylcarbodiimide (DCC), in an appropriate solvent at ambient temperatures. The resultant amide is then treated successively with an appropriate reagent, for example, phosphorous pentachloride/methanol/sodium azide in the presence of an organic base, e.g., pyridine. The reaction is normally carried out in an aprotic solvent under anhydrous conditions.

The overall reactions leading to the compounds of the present invention can be summarized in the following schemes:

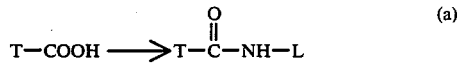

wherein L represents a protecting group, for example, (a) P—methoxybenzyl (PMB)
(b) p-t-butoxycarbonylbenzyl
(c) other appropriately substituted benzyl group.

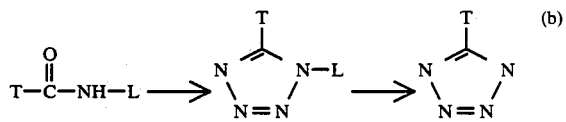

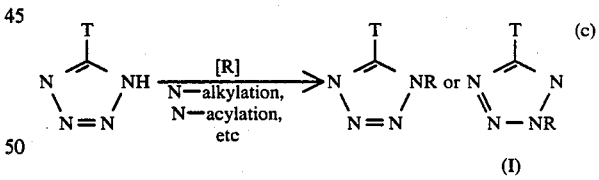

As shown above in scheme (c), once the tetrazolyl structure is constructed, it can be modified via known procedures of N-alkylation, N-arylation or N-acylation to a compound of formula (I).

This invention also relates to a method of treating inflammation in patients using a compound of Formula (I), particularly an especially preferred compound as the active constituent.

It has been found that the compounds of Formula (I) have anti-inflammatory antidegeneration activity and are effective in the prevention and inhibition of edema and granuloma tissue formation as shown below in Table II by the effective inhibition of the proteolytic function of human granulocyte elastase.

TABLE I

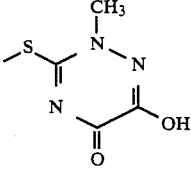

| R¹ | A | R | Q¹ | IC$_{50}$ ($\mu$g/ml) |
|---|---|---|---|---|
| —OCH$_3$ | CH$_3$CO—O— | H | H | 20 |
| " | CH$_3$CO—O— | PMB[a] | H | 0.8 |
| " | φCH$_2$NH—CO—O— | H | H | 4.0 |
| " | φCH$_2$NH—CO—O— | PMB | H | 0.3 |
| " | (CH$_3$)$_2$N—CO—O— | PMB | H | 0.7 |
| " | (CH$_3$)$_2$N—CO—O— | H | H | 2.0 |
| " | CH$_3$CO—O— | —CH$_2$φ[b]—(p-COOt-Bu) | H | 0.8 |
| " | CH$_3$CO—O— | —CH$_2$φ—(p-COOH) | H | 0.8 |
| " | φCH$_2$NH—CO—O— | —CH$_2$φ—(p-COOt-Bu) | H | 0.7 |
| " | φCH$_2$NH—CO—O— | —CH$_2$φ—(p-COOH) | H | 0.7 |
| " | PMB—O—CO—CH$_2$NH—CO—O— | PMB | H | 0.3 |
| —OCH$_3$ | H—O—CO—CH$_2$NH—CO—O— | PMB | H | 0.07 |
| " | H—O—CO—CH$_2$NH—CO—O— | H | H | 5.0 |
| " | CH$_3$—O—CO—CH$_2$NH—CO—O— | PMB | H | 0.8 |
| " | CH$_3$—CO—O— | PMB | —CH$_3$ | 0.1 |
| " | CH$_3$—CO—O— | H | —CH$_3$ | 2.0 |
| " | 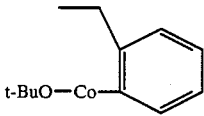 | PMB | H | 2.0 |
| " | " | H | H | 4.0 |
| " | CH$_3$—CO—O— | t-Bu—O—CO—CH$_2$— | H | 15 |
| " | CH$_3$—CO—O— | HO—CO—CH$_2$— | H | 20 |
| " | CH$_3$—CO—O— | 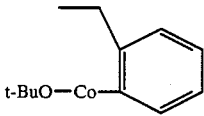 | H | 0.2 |
| " | CH$_3$—CO—O— | PMB | φCH$_2$— | 0.01 |

[a] PMB = p-methoxybenzyl
[b] φ = phenyl

TABLE II

| A | R | Q¹ | IC$_{50}$ ($\mu$g/ml) |
|---|---|---|---|
| CH$_3$—CO—O— | —CH$_2$φ—(p-COO—t-Bu) | H | 0.04 |
| " | —CH$_2$φ—(p-COOH) | H | 0.2 |
| " | —CH$_3$ | H | 0.2 |
| " | —CH$_2$CO—OH | H | 3.0 |
| " | —CH$_2$φ—(o-COO—t-Bu) | H | 0.3 |
| " | —CH$_2$φ—(o-COOH) | H | 0.3 |

TABLE III

| n | IC$_{50}$ (μg/ml) |
|---|---|
| 0 | 2.0 |
| 1 | 2.0 |
| 2 | 0.5 |

| | |
|---|---|
| 0 | 10.0 |
| 2 | 0.2 |

Protocol

Enzyme Assays for the Inhibition of Human Polymorphonuclear Leukocyte Elastase Via Hydrolysis of N-t-Boc-alanyl-alanyl-prolylalanine-p-nitroanilide Reagents:

0.05M TES (N-tris[hydroxymethyl]methyl-2-aminoethanesulfonic acid) Buffer, pH 7.5.

0.2 mM N-t-Boc-alanyl-alanyl-prolyl-alanine-p-nitroanilide (Boc-AAPAN).

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors (cephalosporin sulfone esters) to be tested dissolved in DMSO just before use Assay Procedure:

To 1.0 ml of 0.2 mM Boc-AAPAN in a cuvette, 0.01–0.1 ml of DMSO with or without inhibitor was added. After mixing, a measurement was taken at 410 mμ to detect any spontaneous hydrolysis due to presence of test compound. 0.05 Milliliters of PMN extract was then added and the ΔOD/min at 410 mμ was measured and recorded. Beckman model 35 spectrophotometer was used.

Results:

Results were reported as ED$_{50}$, i.e., effective dosage in micrograms per milliliter (μg/ml) for 50% inhibition of the enzyme activity 2 minutes after zero time.

Comments:

The elastase activity in the crude PMN extract may vary from one preparation to another. A control of each new batch is run, and the volume added in the assay procedure is adjusted according to activity.

Accordingly, the compounds of Formula (I) can be used to reduce inflammation and relieve pain in diseases such as emphysema, rheumatoid arthritis, osteoarthritis, gout, bronchial inflammation, infectious arthritis, rheumatic fever and the like.

For treatment of inflammation, fever or pain, the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium caronate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLE 1

3-Acetoxymethyl-7α-methoxy-4-(tetrazol-5-yl)-3-cephem-1,1-dioxide

Step A: Preparation of 3-acetoxymethyl-7α-methoxy-3-cephem-4-carboxylic acid t-Butyl 3-acetoxymethyl-7α-methoxy-3-cephem-4-carboxylate (9.3 g) was dissolved in precooled trifluoroacetic acid (TFA) (100 ml) and stirred at 0° C. for 1 hour. The volatiles were removed first in vacuo, then under a stream of nitrogen. The residue was taken up in methylene chloride and washed with water and brine, dried over sodium sulfate and evaporated to give 6.5 g of 3-acetoxymethyl-7α-methoxy-3-cephem-4-carboxylic acid.

Step B: Preparation of 3-acetoxymethyl-7α-methoxy-4-[N-(1-p-methoxybenzyl)carbamoyl]-3-cephem 3-Acetoxymethyl-7α-methoxy-3-cephem-4carboxylic acid (6.5 g) was dissolved in dry dioxane (100 ml) and N-hydroxysuccinimide (3.9 g) and dicyclohexylcarbodiimide (DCC) (7.0 g) were added. After 30 minutes, triethylamine (6 ml) was added and after another 15 minutes p-methoxybenzylamine (6.5 ml) in dioxane (10 ml) was added. After 1 hour, the reaction was quenched into a mixture of ethyl acetate and water containing 50 ml of 2N HCl. The layers were separated and the ethyl acetate layer was washed with water, sodium bicarbonate solution and brine, dried over sodium sulfate and evaporated. The residue was flash chromatographed using a solvent gradient of 40 to 60% ethyl acetate/hexane to give 5.6 g of 3-acetoxymethyl-7α-methoxy-[N-(1-p-methoxybenzyl)carbamoyl]-2cephem. NMR (CDCl$_3$): δ=2.05 (s) 3H; 3.52 (s) 3H; 3.81 (s) 3H; 4.2–4.8 (m) 6H; 5.14 (s) 1H; 6.49 (s) 1H; 6.85 (br s) 1H; 7.0 (ABq) 4H.

The procedure described above was repeated using p-t-butoxycarbonylbenzylamine to obtain 3-acetoxymethyl-7α-methoxy-4-[N-(p-t-butoxycarbonylbenzyl)carbamoyl]-2-cephem. NMR (CDCl$_3$) : δ2.07 (s) 3H; 3.52 (s) 3H; 4.45 (dd) 2H; 4.62 (br s) 1H; 4.64 (ABq) 2H; 4.86 (br s) 1H; 5.14 (br s) 1H; 6.50 (br s) 1H; 7.22 (br t ) 1H; 7.36 (d) 2H; 7.98 (d) 2H.

Step C: Preparation of 3-acetoxymethyl-7α-methoxy-4-[1-(p-methoxybenzyl)tetrazol-5-yl]-2-cephem 3-Acetoxymethyl-7α-methoxy-4-[N-(α-methoxybenzyl)carbamoyl]-2-cephem (3.8 g) was dissolved in CDCl$_3$ (60 ml) and cooled in an ice bath under nitrogen. Pyridine (4.5 ml) was added followed by slow addition of phosphorous pentachloride (4.0 g). The reaction was stirred vigorously as it was allowed to warm to room temperature over 1 hour. The reaction was again cooled as pyridine (4.5 ml) and then methanol (4.5 ml) were added. After 15 minutes ammonium chloride (2.5 g) and sodium azide (3.0 g) were added. The reaction was vigorously stirred at room temperature for 2 hours and was then quenched into a mixture of methylene chloride and water containing 50 ml of 2N HCl. The methylene chloride layer was separated, washed with water, sodium bicarbonate solution and brine, dried over sodium sulfate and evaporated. The residue was flash chromatographed using a solvent gradient of 40 to 50% ethyl acetate/hexanes to give 3.0 g of 3-acetoxymethyl-7α-methoxy-4-[1-(p-methoxybenzyl)tetrazol-5-yl]-2-cepham. NMR (CDCl3) : δ1.76 (s) 3H; 3.49 (s) 3H; 4.38 (ABq) 2H; 4.64 (s) 1H; 5.67 (s) 1H; 5.70 (ABq) 2H; 6.64 (s) 1H; 7.15 (ABq) 4H.

The procedure was repeated starting with 3-acetoxymethyl-7α-methoxy-4-[N-(p-butoxycarbonylbenzyl)carbamoyl]-2-cephem to obtain 3-acetoxymethyl-7α-methoxy-4-[1-(p-t-butoxycarbonylbenzyl)tetrazol-5-yl]-2-cephem. NMR (CDCl$_3$) : δ 1.58 (s) 9H; 2.06 (s) 3H; 3.46 (s) 3H; 4.46 (ABq) 2H; 4.59 (s) 1H; 4.61 (s) 1H; 5.81 (br s) 1H; 5.85 (ABq) 2H; 6.67 (br s) 1H; 7.21 (d) 2H; 8.04 (d) 2H.

Step D: Preparation of 3-acetoxymethyl-7α-methoxy-4-[1-(p-methoxybenzyl)tetrazol-5-yl]-2-cephem-1,1-dioxide To a solution of 3-acetoxymethyl-7α-methoxy-4-[1(p-methoxybenzyl)tetrazol-5-yl]-2-cephem (330 mg) in methylene chloride (10 ml) was added 80% m-chloroperbenzoic acid (460 mg). The reaction was stirred at room temperature for 24 hours and then quenched into a solution of sodium bicarbonate and sodium sulfite. The methylene chloride layer was washed with brine and dried over sodium sulfate. Pyridine (2 drops) was added to convert the 2-cephem product completely to the 3-cephem and the solvent was evaporated. The product was recrystallized from ethyl acetate/hexane to give 240 mg of 3-acetoxy- methyl-7α-methoxy-4-[1-(α-methoxybenzyl)tetrazol-5-yl]-3-cephem-1,1-dioxide. NMR (CDCl$_3$): δ2.00 (s) 3H; 3.57 (s) 3H; 3.82 (s) 3H; 3.84 (ABq) 2H; 4.06 (ABq) 2H; 4.68 (br s) 1H; 5.21 (d) 1H; 5.56 (br s) 1H; 7.08 (ABq) 4H.

The procedure was repeated starting with 3-acetoxymethyl-7α-methoxy-4-[N-(p-t-butoxycarbonylbenzyl)tetrazol-5-yl]-2-cephem to give 3-acetoxymethyl-7α-methoxy-4-[1-(p-t-butoxycarbonylbenzyl)tetrazol-5-yl]-2-cephem-1,1-dioxide, NMR (CDCl$_3$) δ 1.60 (s) 9H; 1.98 (s) 3H; 3.56 (s) 3H; 3.88 (ABq) 2H; 4.18 (ABq) 2H; 4.68 (br s) 1H; 5.20 (d) 1H; 5.64 (s) 2H; 7.44 (d) 2H; 8.05 (d) 2H.

Step E: Preparation of 3-acetoxymethyl-7α-methoxy-4-(tetrazol-5-yl)-3-cephem-1,1-dioxide A solution of 3-acetoxymethyl-7α-methoxy-4[1-(α-methoxybenzyl)tetrazol-5-yl]-3-cephem-1,1-dioxide (200 mg) in TFA (5 ml) and anisole (1 ml) was heated at 45°-50° C. for 2 hours. The volatiles were removed in vacuo then in a nitrogen stream. The residue was taken up in methylene chloride and extracted with dilute sodium bicarbonate. The aqueous layer was acidified with 2N HCl to pH 2-3 in the presence of ethyl acetate. The ethyl acetate layer was separated, washed with brine, dried over sodium sulfate and evaporated. The residue was triturated with ether and filtered to give 120 mg of 3-acetoxymethyl-7α-methoxy-4-(tetrazol-5-yl)-3-cephem-1,1-dioxide. NMR (acetone-d$_6$): δ 2.04 (s) 3H; 3.63 (s) 3H; 4.33 (ABq) 2H; 4.92 (ABq) 2H; 5.30 (d) 1H; 5.46 (br s) 1H.

EXAMPLE 2

3-Acetoxymethyl-7α-methoxy-4-[2-(p-t-butoxycarbonyl- benzyl)tetrazol-5-yl]-3-cephem-1,1-dioxide To a solution of 3-acetoxymethyl-7α-methoxy-4-(tetrazol-5-yl)-3-cephem (200 m ) in DMF (5 ml) was added ethyldiisopropylamine (200 μl), sodium iodide (10 mg) and p-(t-butoxycarbonyl)benzyl bromide (300 mg). After 4 hours, the reaction was poured into ether and washed with dilute HCl solution, water, sodium bicarbonate solution and brine, dried over sodium sulfate and evaporated. The residue was purified on 2×1000 μm preparative thin layer plates eluting with 50% ethyl acetate/hexanes to give a mixture of isomers. The desired isomer was separated on preparative thin layer plates using 15% ethyl acetate/methylene chloride to afford 180 mg of 3-acetoxymethyl-7α-methoxy-4-[2-(p- t-butoxycarbonylbenzyl)tetrazol-5-yl]-3-cephem-1,1-dioxide. NMR (CDCl$_3$): δ 1.60 (s) 9H; 2.06 (s) 3H; 3.62 (s) 3H; 3.98 (ABq) 2H; 4.80 (ABq) 2H; 4.90 (br s) 1H; 5.22 (d) 1H; 5.88 (ABq) 2H; 7.42 (d) 2H; 8.04 (d) 2H.

EXAMPLE 3

3-Acetoxymethyl-7α-methoxy-4-[2-(α-hydroxycarbonyl-benzyl)tetrazol-5-yl]-3-cephem-1,1-dioxide 3-Acetoxymethyl-7α-methoxy-4-[2-(p-t-butoxycarbonylbenzyl)tetrazol-5-yl]-3-cephem-1,1-dioxide (160 mg) was dissolved in anisole (0.5 ml) and precooled TFA (10 ml) and stirred at 0° C. for 1 hour. The volatiles were removed in vacuo and the residue purified on 2×1000 μm preparative TLC plates eluting with 1% acetic acid in 1:1 ethyl acetate/ hexanes to give 120 mg of 3-acetoxymethyl-7α-methoxy-4-[2-(p-hydroxycarbonylbenzyl)tetrazol-5-yl]-3-cephem-1,1-dioxide. NMR (acetone-d$_6$): δ 2.00 (s) 3H; 3.60 (s) 3H; 4.28 (ABq) 2H; 4.80 (ABq) 2H; 5.24 (d) 1H; 5.42 (br s) 1H; 6.15 (s) 2H; 7.54 (br s) 2H; 8.10 (br s) 2H.

The procedure was repeated using 3-acetoxymethyl-7α-methoxy-4-[1-(p-t-butoxycarbonylbenzyl)tetrazol-5-yl]-3-cephem-1,1-dioxide to obtain 3-acetoxymethyl-7α-methoxy-4-[1-(p-hydroxycarbonylbenzyl)tetrazol-5-yl]-3-cephem-1,1-dioxide. NMR (acetone-d6); δ 1.98 (s) 3H; 3.52 (s) 3H; 4.34 (ABq) 2H; 4.46 (ABq) 2H; 5.29 (d) 1H; 5.46 (br s) 1H; 5.86 (s) 2H; 7.56 (d) 2H; 8.06 (d) 2H.

EXAMPLE 4

3-Acetoxymethyl-7α-methoxy-2-methyl-4-(tetrazol-5-yl)-3-cephem-

Step A: Preparation of t-Butyl 3-acetoxymethyl-7α-methoxy-2-methyl-3-cephem-4-carboxylate A solution of t-butyl 3-acetoxymethyl-7α-methoxy-2-methyl-3-cephem-4-carboxylate-1β-oxide (2.36 gm) in dry dimethylformamide (40 ml) at 0° C. was treated with anhydrous stannous chloride (2.3 gm) and acetyl chloride (6.5 ml). After stirring at 0° C. for 30 minutes, the solution was poured into ice water and extracted with ether (3X). The combined extracts were successively washed with water (1X) 1N sodium bicarbonate solution (2X), and saturated salt solution (2X). After drying over anhydrous sodium sulfate, the solvent was removed by rotoevaporation to give t-butyl 3-acetoxymethyl-7α-methoxy-2-methyl-3-cephem-4-carboxylate (2.25 gm), a mixture of (3:1) 2α- and 2β-isomers, as a yellow oil. NMR (CDCl$_3$): δ 1.50, 1.56 (9H, s); 1.52 (3H, d, J=7 Hz), 2.12 (3H, s); 3.57, 3.60 (3H, s); 3.61 (1H, m); 4.60 (1H, d, J=1.5 Hz); 4.76; 4.92 (2H, ABq, J=12Hz); 5.0 (1H, d, J=1.5 Hz).

Step B: Preparation of t-acetoxymethyl-7α-methoxy-2-methyl-(4-tetrazol-5-yl)-3-cephem t-Butyl 3-acetoxymethyl-7α-methoxy-2-methyl-3-cephem-4-carboxylate (2.25 gm) was treated in a similar manner to that of Example 1, Steps A to E to give 3-acetoxymethyl-7α-methoxy-2-methyl-4-(tetrazol-5-yl)-3-cephem (90 mg). NMR (CDCl$_3$): δ 1.68; 1.76 (3H, d, J=7 Hz, 1:3); 2.08; 2.11 (3H, s, 1:3); 3.58 (3H, s); 3.86; 4.20 (1H, q, J=7 Hz, 3:1); 4.82; 4.86 (1H, d, J=12 Hz, 1:3); 5.30 (1H, br d, J=12 Hz); 4.96 (1H, d, J=4.5 Hz); 5.24 (1H, d, J=1.5Hz).

EXAMPLE 5

3-Acetoxymethyl-2-benzyl-7α-methoxy-4-(1-p-methoxy-benzyltetrazol-1-yl)-3-cephem-1,1-dioxide Benzylbromide (0.39 ml) and 60% sodium hydride in oil dispersion (39 mg) was added to a solution of 3-acetoxymethyl-7α-methoxy-4-(1-p-methoxybenzyl-tetrazol-5-yl)-3-cephem-1,1-dioxide (300 mg) in dry dimethylformamide (3 ml) at −50° C. under nitrogen atmosphere. Slowly warmed the solution to 0° C. over 1 hour then poured into saturated ammonium chloride and ice. This mixture was extracted with ethyl acetate (3X). The combined extracts were successively washed with water (3X) and saturated salt solution and dried over anhydrous sodium sulfate. The solvent was removed by rotoevaporation and the residue purified by preparative thin layer chromatography to give 3-acetoxymethyl-2-benzyl-7α-methoxy-4-(1-p-methoxy-benzyl-tetrazol-1-yl-3-cephem-1,1-dioxide (80 mg) as a glassy solid. NMR (CDCl$_3$): δ 1.88 (3H, s); 3.30 (3H, s); 3.03; 3.40 (2H, dABq, J=16.4 Hz); 3.72 (1H, d, J=1.5 Hz); 3.94 (1H, t, J=4 Hz); 4.18-4.40 (2H, m); 5.08 (1H, d, J=1.5 Hz); 5.24; 5.48 (2H, ABq, J=15 Hz), 6.86 (2H, d, J=7 Hz), 7.18-7.40 (7H, m).

EXAMPLE 6

3-Hydroxymethyl-7α-methoxy-4-(1-p-methoxybenzyl-tetrazol-5-yl)-2-cephem

A solution of 2.8 g (6.5 mmol) of 3-acetoxymethyl-7α-methoxy-4-(1-p-methoxybenzyl-tetrazol-5-yl)-2-cephem in 20 ml of 2-propanol was prepared by gentle heating. Titanium (IV) isopropoxide (2 ml, 6.7 mmol) was added to the solution and the flask was heated in a 50°-55° C. bath under nitrogen atmosphere. After 1 hour the reaction mixture was diluted with ethyl acetate and poured into water. The layers were separated and the aqueous layer was extracted with ethyl acetate. The combined ethyl acetate layer was washed with water, saturated NaCl and dried. The concentrated filtrate was chromatographed using 30-40% acetone-hexane to obtain 1.96 g (78% yield) of 3-hydroxymethyl-7α-methoxy-4-(1-p-methoxybenzyl-tetrazol-5-yl)-2-cephem. $^1$H NMR (CDCl$_3$): δ 3.48 (s, 3H); 3.8 (s, 3H); 3.96 (m, 2H); 4.62 (bs, 1H); 4.7 (bs, 1H); 5.64 (bs, 1H); 5.73 (ABq, J=114 Hz, 2H); 6.5 (bs, 1H); 6.93 (d, J=8 Hz, 2H); 7.36 (d, J=8 Hz, 2H).

EXAMPLE 7

3-(N-benzylcarbamoyloxymethyl)-7α-methoxy-4-(1-p-methoxybenzyl-tetrazol-5-yl)-2-cephem Benzyl isocyanate (0.21 ml, 1.7 mmol) was added to a solution of 0.45 g (1.16 mmol) of 3-hydroxymethyl-7α-methoxy-4-(1-p-methoxybenzyltetrazol-5-yl)-2-cephem in 3 ml of dichloromethane. 4-Dimethylaminopyridine (3 mg) was added and the solution was heated to reflux. After 1.5 hours, the reaction mixture was diluted with dichloromethane and poured into water. The layers were separated and the aqueous layer was extracted with dichloromethane. The combined organic layer was washed with NaHCO$_3$ solution, saturated NaCl solution and dried. The filtrate was concentrated and the residue was chromatographed using 20-50% ethyl acetate-hexane to obtain 0.34 (56% yield) of 3-(N-benzylcarbamoyloxymethyl)-7α-methoxy-4-[1-p-methoxybenzyl-tetrazol-5-yl)2-cephem. $^1$H NMR (CDCl$_3$)δ 3.48 (s, 3H), 3.67 (s, 3H); 4.1-4.7 (m, 6H); 5.68 (bs, 1H); 5.72 (ABq, J=14 Hz, 2H); 6.64 (bs, 1H); 6.88 (d, J=8 Hz, 2H); 7.2-7.5 (m, 7H).

EXAMPLE 8

3-(N-benzyl-carbamoyloxy-methyl)-7α-methoxy-4-(1-p-methoxybenzyl-tetrazol-5-yl)-3-cephem-1,1-dioxide Following the procedure outlined in Step D of Example 1, 0.34 g of 3-(N-benzyl-carbamoyloxymethyl)-7α-methoxy-4-(1-p-methoxybenzyl-tetrazol-5-yl)-2-cephem was converted to 0.3 g of 3-(N-benzylcarbamoyloxy-methyl)-7α-methoxy-4-(1-p-methoxybenzyl- tetrazol-5-yl)-3-cephem-1,1-dioxide. $^1$H NMR (Acetone-$d_6$) δ 3.53 (s, 3H); 3.82 (s, 3H); 4.1–4.6 (m, 6H); 5.28 (d, J=2 Hz, 1H); 5.46 (bs, 1H); 5.61 (bs, 2H); 6.96 (d, J=8 1 Hz, 2H); 7.3–7.5 (m, 7H).

EXAMPLE 9

3-(N-Benzyl-carbamoyloxy-methyl)-7α-methoxy-4-(1H-tetrazol-5-yl)-3-cephem-1,1-dioxide 3-(N-Benzyl-carbamoyloxy-methyl)-7α-methoxy-4-(1-p-methoxybenzyl-tetrazol-5-yl)-3-cephem-1,1-dioxide (110 mg) was treated in a manner similar to Step E of Example 1 to give 43 mg of 3-(N-benzyl- carbamoyloxy-methyl)-7α-methoxy-4-(1H-tetrazol-5-yl)-3-cephem-1,1-dioxide. $^1$HNMR (Acetone-$d_6$): δ 3.62 (s, 3H); 4.1–4.6 (m, 4H); 4.92 (ABq, J=13 Hz, 2H); 5.28 (bs, 1H); 5.47 (bs, 1H); 7.0 (bs, 1H); 7.36 (m, 5H).

EXAMPLE 10

3-Chloromethyl)-7α-methoxy-4-(1-p-methoxybenzyl-tetrazol-5-yl)-3-cephem-1,1-dioxide A solution of 1.71 g (4.4 mmol) of 3-hydroxymethyl-α-methoxy-4-(1p-methoxybenzyl-tetrazol-5-yl)2-cephem in 20 ml of tetrahydrofuran and 1.1 ml of pyridine was cooled in an ice-bath. Thionyl chloride (0.5 ml, 6.4 mmol) was added to the solution dropwise over 5 minutes. After stirring for 15 minutes, the reaction mixture was diluted with ethyl acetate and poured into cold water. The layers were separated and the aqueous layer was extracted with ethyl acetate. The combined ethyl acetate layer was washed with NaHCO$_3$ solution, water, 1.2N HCl, saturated NaCl and dried. The filtrate was concentrated to obtain 1.54 of residue.

The residue was dissolved in 15 ml of dichloromethane and 1.51 g (80%, 7 mmol) of m-chloroperoxybenzoic acid was added in portions. After stirring the reaction mixture overnight, it was diluted with dichloromethane and poured into NaHCO$_3$ solution. The layers were separated and the aqueous layer was extracted with dichloromethane. The organic layers were combined. It was washed with aqueous Na$_2$SO$_3$, saturated NaCl and dried. The filtrate was concentrated and the residue was dissolved in hot dichloromethane. The solution was filtered. The filtrate was cooled and 30% ethyl acetate-hexane was added to initiate crystallization. The resultant yellow crystals were filtered and dried to obtain 0.77 g of 3-chloromethyl-7α-methoxy-4-(1-p-methoxybenzyl-tetrazol-5-yl)-3-cephem-1,1-dioxide. $^1$HNMR (CDCl$_3$)δ3.58 (s, 3H); 3.82 (s, 3H); 3.5–4.2 (m, 4H); 4.66 (bs, 1H); 5.2 (d, J=2 Hz, 1H); 5.57 (ABq, J=14 Hz, 2H); 6.92 (d, J=8 Hz, 2H); 7.25 (d, J=8 Hz, 2H).

EXAMPLE 11

7α-Methoxy-3-[(1,2,5,6-tetrahydro-5,6-dioxo-2-methyl-as-triazin-3-yl)thio]methyl -4-(1-p-methoxy-benzyl-tetrazol-5-yl)-3-cephem-1,1-dioxide A solution of 78 mg (0.48 mmol) of 1,2,5,6-tetrahydro-5,6-dioxo-3-mercapto-2-methyl-as-triazine in 1.5 ml of water was prepared by adding 85 mg (1 mmol) of NaHCO$_3$. A solution of 210 mg (0.48 mmol) of 3-chloromethyl-7α-methoxy-4-(1-p-methoxybenzyl-tetrazol-5-yl)-3-cephem-1,1-dioxide in 3 ml of acetone was added to it. After stirring the reaction mixture overnight under nitrogen, the dark yellow solution was concentrated. The residue was diluted with 7% NaHCO$_3$ solution and washed with ether. The aqueous solution was neutralized with concentrated HCl in the presence of ethyl acetate. The layers were separated and the aqueous layer was extracted with ethyl acetate. The combined ethyl acetate layer was washed with water, saturated NaCl and dried. The filtrate was concentrated. The residue was recrystallized from ethyl acetate to obtain 168 mg (63% yield) of 7α-methoxy-3-[[(1,2,5,6-tetrahydro-5,6-dioxo-2-methyl-as-triazin-3-yl)thio]methyl]-4-(1-p-methoxybenzyl-tetrazol-5-yl)-3-cephem-1,1-dioxide. $^1$HNMR (Acetone-$d_6$) δ 3.56 (s, 3H); 3.77 (s, 3H); 3.83 (s, 3H); 4.0–4.7 (m, 4H); 5.29 (bs, 1H); 5.48 (bs, 1H); 5.72 (m, 2H); 6.97 (d, J=8 Hz, 2H); 7.43 (d, J=8 Hz, 2H).

EXAMPLE 12

7α-Methoxy-3-[[(1,2,5,6-tetrahydro-5,6-dioxo-2-methyl-as-triazin-3-yl)thio]methyl]-4-(1H-tetrazol-5-yl)-3-cephem-1,1-dioxide To 70 mg (0.12 mmol) of 7α-methoxy-3[[(1,2,5,6-tetrahydro-5,6-dioxo-2-methyl-as-triazin-3yl)thio]methyl]-4-(1-p-methoxybenzyl-tetrazol-5-yl)-3-cephem-1,1-dioxide was added 2.5 ml of cold trifluoroacetic acid and 0.5 ml of anisole. The solution was heated in a 55° bath under nitrogen. After 1.5 hours the dark solution was cooled and concentrated in vacuo. The residue was dissolved in NaHCO$_3$ solution and ether. The layers were separated and the organic layer was extracted with NaHCO$_3$ solution. The combined aqueous layer was washed with ether. The aqueous layer was neutralized with concentrated HCl in the presence of ethyl acetate. The layers were separated and the aqueous layer was extracted with ethyl acetate. The combined organic layer was washed with saturated NaCl and dried. The filtrate was concentrated in vacuo. The residue was chromatographed on a reverse phase C-18 HPLC column using 30% acetonitrile-water containing 0.2% trifluoroacetic acid to obtain 37 mg (67% yield) of 7α-methoxy-3[[(1,2,5,-tetrahydro-5,6-dioxo-2-methyl-as-triazin-3-yl)thio]methyl]-4-(1H-tetrazol-5-yl)-3-cephem-1,1-dioxide as a pale yellow solid. $^1$H NMR (Acetone-$d_6$) δ 3.56 (s, 3H); 3.74 (s, 3H); 3.9–4.7 (m, 4H); 5.24 (s, 1H); 5.32 (bs, 1H); 4.8–5.5 (broad, 2H).

EXAMPLE 13

3-(N-Benzyl-carbamoyloxy-methyl)-7α-methoxy-4-(1H- tetrazol-5-yl)-3-cephem-1,1-dioxide Step A: Preparation of N-(2,4-dimethoxybenzyl)-3-acetoxymethyl-7α-methoxy-2-cephem-4-carboxamide Cold trifluoracetic acid (20 ml) and anisole (5 ml) were added to 2.82 g (8.2 mmol) of 3-acetoxy- methyl-7- methoxy-3-cephem-4-carboxylic acid t-butyl ester. The solution was cooled in an ice-bath. After 0.5 hour, trifluoroacetic acid was removed in vacuo, keeping the bath temperature below 35°. The residue was dissolved in 7% $NaHCO_3$ solution and washed with ether. The aqueous layer was acidified to pH 2 with concentrated HCl in the presence of ethyl acetate. The layers were separated and the aqueous layer was extracted with ethyl acetate. The combined organic layer was washed with water, saturated NaCl and dried. The filtrate was concentrated.

The residue was dissolved in 20 ml of dioxane and 1.15 g (10 mmol) of N-hydroxysuccinimide and 2.06 g (10 mmol) of DCC were added. The solution was vigorously stirred. After 15 minutes, 2.1 ml (15 mmol) of triethylamine was added. After 30 minutes a suspension containing 2.4 g (11.8 mmol) of 2,4dimethoxybenzylamine and 2.1 ml (15 mmol) of triethylamine in 5 ml of dioxane was added. After 1.5 hours, the reaction mixture was diluted with ethyl acetate and 1.2N HCl. The solution was filtered and the filtrate was partitioned. The aqueous layer was extacted with ethyl acetate. The organic layers were combined. It was washed with water, $NaHCO_3$ solution, saturated NaCl and dried. The filtrate was concentrated and the residue was chromatographed on a flash column using 30–50% ethyl acetate/hexane. N-(2,4-dimethoxybenzyl)-3-acetoxymethyl-7α-methoxy-2-cephem-4-carboxamide (1.75 g, 48% yield) was obtained as a yellow oil. $^1HNMR$ ($CDCl_3$) δ 2.03 (s, 3H); 3.5 (s, 3H); 3.81 (s, 3H); 3.84 (s, 3H); 4.2-4.8 (m, 5H); 4.79 (s, 1H); 5.08 (s, 1H); 6.4–6.5 (m, 3H); 6.88 (brs, 1H); 7.17 (d, J=7 Hz, 1H).

Step B: Preparation of 3-acetoxymethyl-7α-methoxy-4-(1-(2,4-dimethoxybenzyl)tetrazol-5-yl)-2-cephem To a solution of 1.75 g (3.9 mmol) of N-(2,4-dimethoxybenzyl)-3-acetoxy-7α-methoxy-2-cephem-4carboxamide in 25 ml of chloroform were added 2 ml of pyridine and 1.66 g (8 mmol) of phosphorous pentachloride. The solution was vigorously stirred. After 1 hour all phosphorous pentachloride had dissolved. The flask was cooled in an ice bath and 2 ml of pyridine and 3.5 ml of methanol were added. The solution was allowed to warm to room temperature in 15 minutes. Sodium azide (1.3 g, 20 mmol) and $NH_4Cl$ (1.07 g, 20 mmol) were added. After vigorously stirring the reaction mixture for 1 hour, it was diluted with dichloromethane and the solution was poured into 1.2N HCl. The layers were separated and the aqueous layer was extracted with dichloromethane. The combined organic layer was washed with water, $NaHCO_3$ solution, saturated NaCl and dried. The filtrate was concentrated. The residue was chromatographed on a flash column using 50–60% ethyl acetate-hexane to obtain 1.17 g (65% yield) of 3-acetoxymethyl-7α-methoxy-4-(1-(2',4'-dimethoxybenzyl)tetrazol-5-yl)-2-cephem. $^1HNMR$ ($CDCl_3$) δ 1.85 (s, 3H); 3.49 (s, 3H); 3.82 (s, 3H); 3.84 (s, 3H); 4.28 (d, J=13 Hz, 1H); 4.54 (d, J=13 Hz, 1H); 4.64 (s, 1H); 4.75 (s, 1H); 5.66 (s, 2H); 5.9 (s, 1H); 6.5–6.6 (m, 2H); 6.65 (s, 1H); 7.32 (d, J=7 Hz, 1H).

Step C: Preparation of 3-hydroxymethyl-7α-methoxy-4-[1-(2',4'-dimethoxybenzyl)tetrazol-5-yl]-2-cephem A solution of 1.17 g (2.5 mmol) of 3-acetoxymethyl-7α-methoxy-4-[1-(2',4'-dimthoxybenzyl)tetrazol-5-yl]-2-cephem in 20 ml of 2-propanol was prepared by gentle heating. Titanium (IV) isopropoxide (0.8 ml, 2.7 mmol) was added to the solution and the flask was heated in a 50°–55° bath under nitrogen atmosphere. After 1 hour the reaction mixture was diluted with ethyl acetate and poured into water. The layers were separated and the aqueous layer was extracted with ethyl acetate. The combined ethyl acetate layer was washed with water, saturated NaCl and dried. The concentrated filtrate was chromatographed on a flash column using 50–60% ethylacetate-hexane to obtain 0.65 g (62% yield) of 3-hydroxymethyl-7α-methoxy-4-[1-(2,4-dimethoxybenzyl)tetrazol-5-yl]-2-cephem. $^1HNMR$ ($CDCl_3$) δ 3.48 (s, 3H); 3.82 (s, 3H); 3.84 (s, 3H); 4.0 (m, 2H); 4.62 (s, 1H); 4.76 (s, 1H); 5.66 (ABq, J=16 Hz, 2H); 6.04 (s, 1H); 6.5-6.6 (m, 3H); 7.32 (d, J=7 Hz, 1H).

Step D: Preparation of 3-(N-benzyl-carbamoyloxymethyl)-7α-methoxy-4-[1-(2',4'-dimethoxybenzyl)tetrazol-5-yl]-3-cephem-1,1-dioxide To a solution of 0.65 g (1.5 mmol) of 3-hydroxymethyl-7α-methoxy-4-[1-(2',4'-dimethoxybenzyl)tetrazol-5-yl]-2-cephem in 6 ml of dichloromethane were added 0.44 ml (3.5 mmol) of benzyl isocyanate and 3 mg of 4-dimethylaminopyridine. The solution was heated to reflux. After 3 hours, the reaction mixture was cooled and diluted with dichloromethane. It was washed with water, $NaHCO_3$ solution, saturated NaCl and dried. Concentration of filtrate gave 1.05 g of residue.

The residue was dissolved in 15 ml of dichloromethane and 1.5 g (80%, 6.9 mmol) of m-chloroperbenzoic acid was added in portions. After stirring the mixture overnight it was poured into $NaHCO_3$ solution containing excess $Na_2SO_3$. The layers were separated and the aqueous layer was extracted with dichloromethane. The combined organic layer was washed with water, saturated NaCl and dried. The concentrated filtrate was chromatographed on a flash column using 50–60% ethyl acetate-hexane to obtain 0.19 g (22% yield) of 3-(N-benzylcarbamoyloxymethyl)-7α-methoxy-4-[1-(2',4'-dimethoxybenzyl)tetrazol-5-yl]-3-cephem-1,1-dioxide. $^1HNMR$ ($CDCl_3$): δ 3.5 (s, 3H); 3.68 (s, 3H); 3.78 (s, 3H); 3.9-4.4 (m, 6H); 4.68 (s, 1H); 5.04 (broad, 1H); 5.14 (s, 1H); 5.54 (s, 2H); 6.4–6.55 (m, 2H); 7.1–7.4 (m, 6H).

Step E: Preparation of 3-(N-benzyl-carbamoyloxymethyl)-7α-methoxy-4-(1H-tetrazol-5-yl)-3 cephem-1,1-dioxide Cold trifluoroacetic acid (2 ml) and anisole (0.5 ml) were added to 90 mg (0.19 mmol) of 3-(N-benzyl-carbamoyloxy-methyl)-7α-methoxy-4-[1-(2',4'-dimethoxybenzyl)-tetrazol-5-yl]-3-cephem-1,1-dioxide. After stirring for 0.5 hour the reaction mixture was concentrated and the residue was dissolved in $NaHCO_3$ solution. It was washed with ether. The aqueous layer was acidified to pH 2 with concentrated HCl in the presence of ethyl acetate. The layers were separated and the aqueous layer was extracted with ethyl acetate. The combined ethyl acetate layer was washed with saturated NaCl and dried. The filtrate was concentrated and the residue was triturated with ether. The white solid was filtered and washed to obtain 37 mg (45% yield) of 3-(N-benzyl-carbamoyloxymethyl)-7α-methoxy-4-(1H-tetrazol-5-yl)-3-cephem-1,1-dioxide. $^1HNMR$ (Acetone-$d_6$) δ 3.62 (s, 3H); 4.1-4.6 (m, 4H); 4.92 (ABq, J=13 Hz, 2H); 5.28 (bs, 1H); 5.47 (s, 1H); 7.0 (brs, 1H); 7.36 (m, 5H).

What is claimed is:

1. A pharmaceutical composition for treating or managing elastase mediated conditions in a mammalian species comprising a non-toxic pharmaceutical carrier and an effective amount of a compound of structural formula:

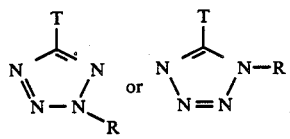 (I)

wherein T is

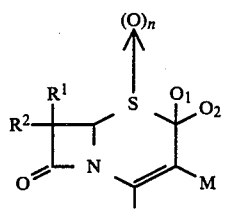

wherein
n is an integer of 0 to 2;
M is
(1) trifluoromethyl;
(2) chloro of fluoro;
(3) —COOH;
(4) —CH₂A wherein A represents:
  (a) R$_a$CO—O— wherein R$_a$ represents
    (1) H;
    (2) straight or branched chain alkyl having from 1 to 6 carbon atoms;
    (3) phenyl;
    (4) cycloalkyl having from 3 to 8 carbon atoms;
    (5) alkenyl having from 2 to 6 carbon atoms;
    (6) phenyl C$_{1-6}$alkyl;
    (7) halo C$_{1-6}$alkyl;
the above groups (1) to (7) can be unsubstituted or substituted with one or more radicals selected from the group consisting of hydroxy, nitro, C$_{1-6}$ alkanoyloxy, halo, cyano, carboxy,

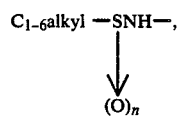

carbamoyl,

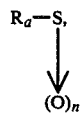

carbamoyloxy, carboxamido, amino, monoalkyl amino or dialkylamino;
  (b) R$_a$R$_b$NCO—O— wherein R$_b$ is defined as R$_a$ and can be the same as or different from R$_a$;
  (c) R$_a$COCH₂NR$_b$—CO—O—;
  (d)

or
  (e) phenoxy;

R¹ is
(1) C$_{1-6}$ alkyl;
(2) —OR$_a$;
(3)

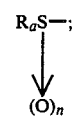

(5) hydrogen; or
(6) phenyl;
R² is
(1) H;
(2) C$_{1-6}$ alkyl; or
(3) benzyl as defined below;
Q¹ and Q² independently are:
(1) hydrogen;
(2) C$_{1-6}$alkyl;
(3) benzyl as defined below;
R is:
(a) H;
(b) phenyl of formula

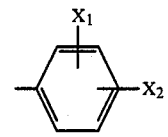

wherein X₁ and X₂ are as defined below;
(c) benzyl of formula:

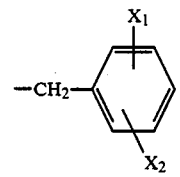

wherein X₁ X₂ independently are H, OC$_{1-6}$alkyl, —COOH, C$_{1-6}$alkyl, —CH₂COOC$_{1-6}$ alkyl;
(d) C$_{1-6}$alkyl;
(e) —CH₂COOH; or
(f) —CH₂COOt Bu.

2. The composition of claim 1 wherein:
M is
(1) trifluoromethyl;
(2) chloro or fluoro; or
(3) —CH₂A wherein A represents:
  (a) R$_a$—CO—O— wherein R$_a$ is as defined below;
  (b) R$_a$NH—CO—O—;
  (c) R$_a$O—CO—CH₂NH—CO—O—; or
  (d) R$_a$—S—;
R¹ is
(1) C$_{1-6}$alkyl;
(2) hydroxy;
(3) OR$_a$ where R$_a$ is
  (a) C$_{1-6}$alkyl;
  (b) —C$_6$H$_5$;
  (c) —CH₂C$_6$H$_5$;
  (d) —CH₂CH₂C$_6$H$_5$;
  (e)

10 where $R_h$ represents hydrogen, $C_{1-6}$alkyl, phenyl, benzyl, or $C_{1-6}$alkylamino; or (6) —$SO_2R_h$;
(7) phenyl; or
(8) halo$C_{1-6}$alkyl—CO—NH—;

$R^2$ is H;

$Q^1$ and $Q^2$ independently are:
(1) hydrogen;
(2) methyl, ethyl or i-or n-propyl;
(3) methylene;
(4) phenylthiomethyl or phenyl sulfonylmethyl;
(5) benzyl of formula

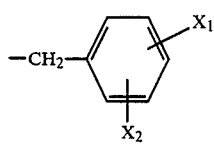

wherein $X_1$ and $X_2$ independently are H, $OCH_3$, —COOH, $C_{1-6}$alkyl, —COO$C_{1-6}$alkyl, —CH$_2$COOH, or $CH_2COOC_{1-6}$alkyl; or
(6) —$CH_2$—CO—O$R_h$; and R is
(1) H;
(2) $CH_3$;
(3) $CH_2COOH$;
(4) benzyl of formula

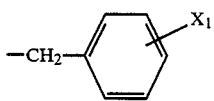

where $X_1$ represents $OCH_3$, —COOH, or —COOt—Bu; or
(5) —$CH_2$COOt-Bu.

3. A compound of formula:

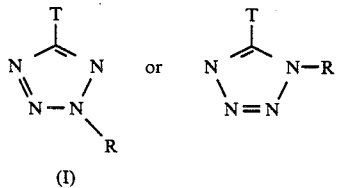

wherein T is

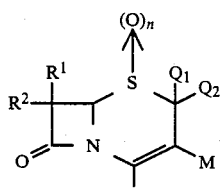

wherein n is an integer of 0 to 2;
M is
(1) trifluoromethyl;
(2) chloro of fluoro;

(3) —COOH;
(4) —$CH_2A$ wherein A represents:
 (a) $R_aCO$—O— wherein $R_a$ represents
  (1) H;
  (2) straight or branched chain alkyl having from 1 to 6 carbon atoms;
  (3) phenyl;
  (4) cycloalkyl having from 3 to 8 carbon atoms;
  (5) alkenyl having from 2 to 6 carbon atoms;
  (6) phenyl $C_{1-6}$alkyl;
  (7) halo $C_{1-6}$alkyl;

the above groups (1) to (7) can be unsubstituted or substituted with one or more radicals selected from the group consisting of hydroxy, nitro, $C_{1-6}$ alkanoyloxy, halo, cyano, carboxy,

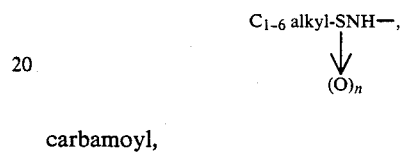

carbamoyl,

carbamoyloxy, carboxyamido, amino, monoalkylamino or dialkylamino;
 (b) $R_aR_bNCO$—O— wherein $R_b$ is defined as $R_a$ and can be the same as or different from $R_a$;
 (c) $R_aCOCH_2NR_b$—CO—O—;
 (d)

or
 (e) phenoxy;

$R^1$ is
(1) $C_{1-6}$ alkyl;
(2) —$OR_a$;
(3)

(5) hydrogen; or
(6) phenyl;

$R^2$ is
(1) H;
(2) $C_{1-6}$ alkyl; or
(3) benzyl as defined below;

$Q^1$ and $Q^2$ independently are:
(1) hydrogen;
(2) $C_{1-6}$alkyl;
(5) benzyl as defined below; or
(6)

R is:
(a) H;
(b) phenyl of formula

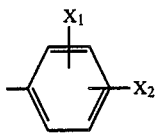

wherein $X_1$ and $X_2$ are as defined below;
(c) benzyl of formula:

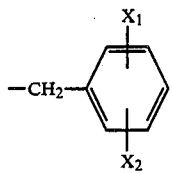

wherein $X_1$, $X_2$ independently are H, $OC_{1-6}$alkyl, —COOH, $C_{1-6}$ alkyl, —$COOC_{1-6}$ alkyl, —$CH_2COOH$, or —$CH_2COOC_{1-6}$ alkyl;
(d) $C_{1-6}$alkyl;
(e) —$CH_2COOH$; or
(f) —$CH_2COOt$—Bu.

4. The compound of claim 3 wherein:
M is
(1) trifluoromethyl;
(2) chloro or fluoro; or
(3) —$CH_2A$ wherein A represents:
  (a) $R_a$—CO—O—; wherein $R_a$ is as defined below
  (b) $R_aHN$—CO—O—;
  (c) $R_aO$—CO—$CH_2NH$—CO—O—; or
  (d) $R_a$—S—;
$R^1$ is
(1) $C_{1-6}$alkyl;
(2) hydroxy;
(3) $OR_a$ where $R_a$ is
  (a) $C_{1-6}$alkyl;
  (b) —$C_6H_5$;
  (c) —$CH_2C_6H_5$;
  (d) —$CH_2CH_2C_6H_5$;
(e)

where $R_h$ represents hydrogen, $C_{1-6}$alkyl, phenyl, benzyl, or $C_{1-6}$alkylamino; or
(5) H;
(6) —$SO_2R_h$; or
(7) phenyl;
(8) halo$C_{1-6}$alkyl—CO—H—;
$R^2$ is H;
$Q^1$ and $Q^2$ independently are:
(1) hydrogen;
(2) methyl, ethyl or i-or n-propyl;
(3) methylene;
(4) phenylthiomethyl or phenyl sulfonylmethyl;
(5) benzyl as previously defined;
(6) —$CH_2$—CO—$OR_h$; and
R is
(1) H;
(2) $CH_3$;
(3) $CH_2COOH$;
(4) benzyl of formula

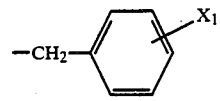

wherein $X_1$ represents $CH_3$, —COOH, or —COOt—Bu; or
(5) —$CH_2COOt$—Bu.

5. The composition of claim 1 wherein the compound is
(a) 3-Acetoxymethyl-7α-methoxy-4-(tetrazol-5-yl)-3-cephem-1,1-dioxide;
(b) 3-Acetoxymethyl-7α-methoxy-4-[2-(p-t-butoxycarbonyl-benzyl)tetrazol-5-yl]-3-cephem-1,1-dioxide;
(c) 3-Acetoxymethyl-7α-methoxy-4-[2-(p-hydroxycarbonyl-benzyl)tetrazol-5-yl]-3-cephem-1,1-dioxide;
(d) 3-Acetoxymethyl-7α-methoxy-2-methyl-4-(tetrazol-5-yl)-3-cephem;
(e) 3-Acetoxymethyl-2-benzyl-7α-methoxy-4-(1-p-methoxy-benzyltetrazol-1-yl)-3-cephem-1,1-dioxide;
(f) 3-Hydroxymethyl-7α-methoxy-4-(1-p-methoxybenzyl-tetrazol-5-yl)-2-cephem;
(g) 3-(N-benzylcarbamoyloxymethyl)-7α-methoxy-4(1-p-methoxybenzyl-tetrazol-5-yl)-2-cephem;
(h) 3-(N-benzyl-carbamoyloxy-methyl-7α-methoxy-4-(1-p-methoxybenzyl-tetrazol-5-yl)-3-cephem-1,1-dioxide;
(i) 3-(N-Benzyl-carbamoyloxy-methyl)-7α-methoxy-4-(1H-tetrazol-5-yl)-3-cephem-1,1-dioxide;
(j) 3-Chloromethyl)-7α-methoxy-4-(1-p-methoxybenzyl-tetrazol-yl)-3-cephem-1,1-dioxide;
(k) 7α-Methoxy-3-[(1,2,5,6-tetrahydro-5,6-dioxo-2-methyl-as-triazin-3-yl)thio]methyl-4-p-methoxy-benzyl-tetrazol-5-yl)-3-cephem-1,1-dioxide;
(l) 7α-Methoxy-3-[[(1,2,5,6-tetrahydro-5,6-dioxo-2-methyl-as-triazin-3-yl)thio]methyl]4(1-H-tetrazol-5-yl)-3-cephem-1,1-dioxide;
(m) 3-(N-Benzyl-carbamoyloxy-methyl)-7α-methoxy-4-(1H-tetrazol-5-yl)-3-cephem-1,1-dioxide.

6. The composition of claim 1 wherein the compound is 3-acetoxy-2-benzyl-7α-methoxy-4-(1-p-methyoxybenzyl-tetrazol-5-yl)-3-cephem-1,1-dioxide.

7. The compound of claim 3 which is
(a) 3-Acetoxymethyl-7α-methoxy-4-(tetrazol-5-yl)-3-cephem-1,1-dioxide;
(b) 3-Acetoxymethyl-7α-methoxy-4-[2-(p-t-butoxycarbonyl-benzyl)tetrazol-5-yl]-3-cephem-1,1-dioxide;
(c) 3-Acetoxymethyl-7α-methoxy-4-[2-(p-hydroxycarbonyl-benzyl)tetrazol-5-yl]-3-cephem-1,1-dioxide;
(d) 3-Acetoxymethyl-7α-methoxy-2-methyl-4-(tetrazol-5-yl)-3-cephem;
(e) 3-Acetoxymethyl-2-benzyl-7α-methoxy-4-(1-p-methoxy-benzyltetrazol-1-yl)-3-cephem-1,1-dioxide;
(f) 3-Hydroxymethyl-7α-methoxy-4-(1-p-methoxybenzyl-tetrazol-5-yl)-2-cephem;
(g) 3-(N-benzylcarbamoyloxymethyl)-7α-methoxy-4-p-methoxybenzyl-tetrazol-5-yl)-2-cephem;
(h) 3-(N-benzyl-carbamoyloxy-methyl-7α-methoxy-4-p-methoxybenzyl-tetrazol-5-yl)-3-cephem-1,1-dioxide;
(i) 3-(N-Benzyl-carbamoyloxy-methyl)-7α-methoxy-4-(1H-tetrazol-5-yl)-3-cephem-1,1-dioxide;
(j) 3-Chloromethyl)-7α-methoxy-4-(1-p-methoxybenzyl-tetrazol-5-yl)-3-cephem-1,1-dioxide;

(k) 7α-Methoxy-3-[(1,2,5,6-tetrahydro-5,6-dioxo-2-methyl-as-triazin-3-yl)thio]methyl-4-(1-p-methoxybenzyl-tetrazol-5-yl)-3-cephem-1,1-dioxide;

(l) 7α-Methoxy-3-[[(1,2,5,6-tetrahydro-5,6-dioxo-2-methyl-as-triazin-3-yl)thio]methyl]4-(1H-tetrazol-5-yl)-3-cephem-1,1-dioxide;

(m) 3-(N-Benzyl-carbamoyloxy-methyl)-7α-methoxy-4-(1H-tetrazol-5-yl)-3-cephem-1,1-dioxide.

8. The compound of claim 3 which is 3-acetoxy-2-benzyl-7α-methoxy-4-(1-p-methoxybenzyl-tetrazol-5-yl)-3-cephem1,1-dioxide.

* * * * *